(12) United States Patent
Fishler (10) Patent No.: US 6,456,877 B1
(45) Date of Patent: Sep. 24, 2002

(54) MULTIELECTRODE DEFIBRILLATOR OR CARDIOVERTING DEVICE WITH SIMPLIFIED DESIGN

(75) Inventor: Matthew G. Fishler, Ithaca, NY (US)

(73) Assignee: Pacesetter, Inc., Sunnyvale, CA (US)

( * ) Notice: Subject to any disclaimer, the term of this patent is extended or adjusted under 35 U.S.C. 154(b) by 62 days.

(21) Appl. No.: 09/633,799

(22) Filed: Aug. 7, 2000

(51) Int. Cl.[7] .................................................. A61N 1/18
(52) U.S. Cl. ........................................................ 607/5
(58) Field of Search ............................... 607/4, 5, 8, 74

(56) References Cited

U.S. PATENT DOCUMENTS

| | | | | |
|---|---|---|---|---|
| 4,953,551 A | * | 9/1990 | Mehra et al. | |
| 5,199,429 A | * | 4/1993 | Kroll et al. | |
| 5,948,004 A | * | 9/1999 | Weijand et al. | 607/72 |
| 5,968,080 A | * | 10/1999 | Brewer et al. | 434/272 |
| 6,047,211 A | * | 4/2000 | Swanson et al. | |
| 6,263,239 B1 | * | 7/2001 | Brewer et al. | 607/5 |
| 6,411,846 B1 | * | 6/2002 | Brewer et al. | 607/5 |

* cited by examiner

*Primary Examiner*—Mark Bockelman
(74) *Attorney, Agent, or Firm*—Steven M. Mitchell (57) ABSTRACT

A circuit for sequentially discharging two capacitors configured for independent discharge into heart electrodes to create a biphasic electrical shock. Upon determination that a therapeutic shock needs to be applied to a heart, the capacitors are charged. Once the capacitors are sufficiently charged, one of the capacitors is switched such that it begins to discharge into the heart. At an appropriate time, this capacitor is switched again such that it no longer discharges into the heart. At this time, the other capacitor is switched such that it begins to discharge into the heart, and at an appropriate time, it is switched such that is stops discharging into the heart. The two capacitors are preferably configured with opposite polarities so that the waveform applied to the heart by the sequential discharging of the two capacitors is biphasic.

7 Claims, 6 Drawing Sheets

MULTIELECTRODE DEFIBRILLATOR OR CARDIOVERTING DEVICE WITH SIMPLIFIED DESIGN

BACKGROUND OF THE INVENTION

1. Field of the Invention

The present invention is directed to a discharge circuit for use in a multielectrode defibrillator or cardioverting device and methods of using such a circuit.

2. Background

Cardiac devices for treating electrical malfunctions of a heart are known. These devices operate by delivering an electrical shock to the heart, which typically stimulates the heart and causes it to begin beating normally. Various devices have been developed over the years for treating a variety of different malfunctions. Some such devices are designed to monitor the heart and deliver a therapeutic shock automatically upon detection of a malfunction. Other devices operate manually, delivering a shock only upon intervention by a user.

One cardiac device is a defibrillator. A defibrillator delivers a relatively large electric shock to a heart that is in fibrillation. Early defibrillators delivered a monophasic shock to the heart. In a monophasic shock, the polarity of the voltage remains the same throughout the shock. It was soon discovered, however, that a biphasic shock can be more effective in treating fibrillation than a monophasic shock. In a biphasic shock, a first portion of the waveform applied to the heart has a first polarity and a second portion of the waveform has an opposite polarity. Typically, a biphasic shock is able to defibrillate a heart with less energy and/or voltage than a monophasic shock.

Figure 1:
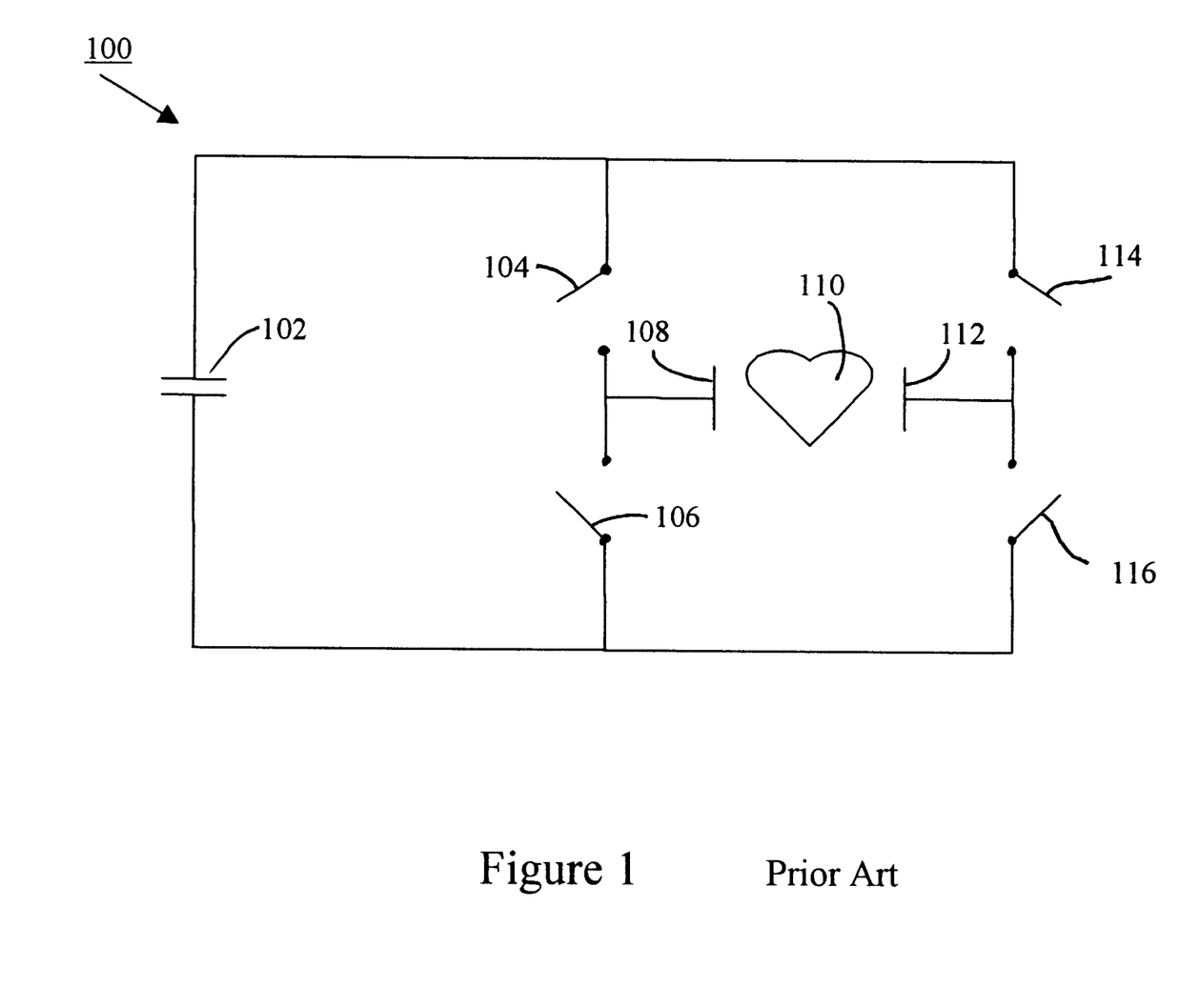
FIG. 1 is a circuit diagram of a prior art circuit for creating a biphasic discharge into a heart.

Known circuits for delivering a biphasic shock utilize either a single discharge capacitor or two discharge capacitors configured to act as a single capacitor. An example of the former circuit is shown in FIG. 1. As shown in FIG. 1, four switches 104, 106, 114, and 116 control the discharge of capacitor 102 through electrodes 108 and 112 into heart 110. Upon determination that a defibrillating shock needs to be delivered to heart 110, a charging circuit (not shown) charges capacitor 102. When capacitor 102 is sufficiently charged, switches 104 and 116 are closed, while switches 106 and 114 remain open. Capacitor 102 begins to discharge, creating a current that flows from electrode 108 to electrode 112. When capacitor 102 has only partially discharged, switches 104 and 116 are opened. Shortly thereafter, switches 106 and 114 are closed. Capacitor 102 then continues to discharge, but this time current flows from electrode 112 to electrode 108. The circuit shown in FIG. 1 is commonly referred to as an "H" bridge.

Figure 2:
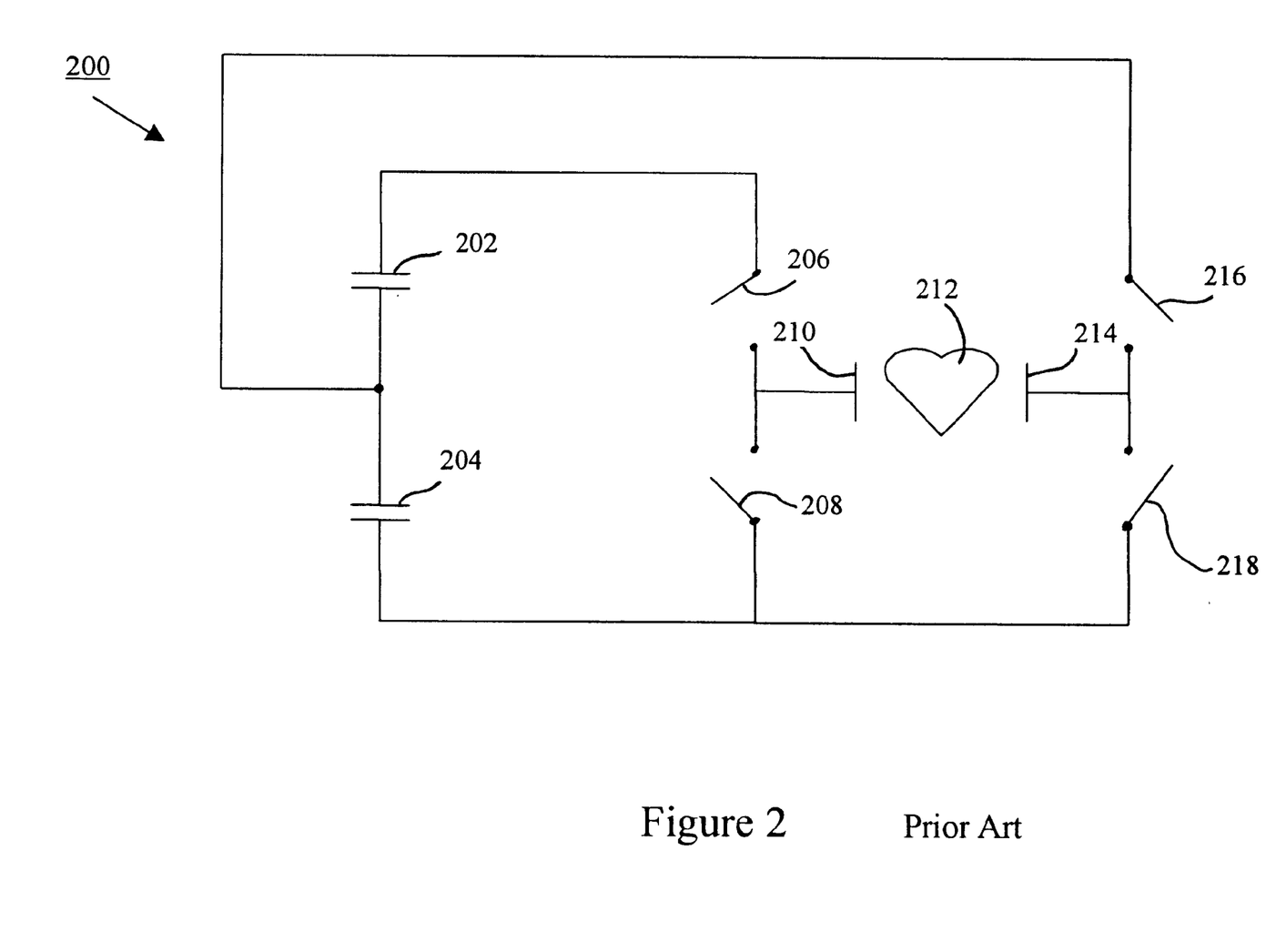
FIG. 2 is a circuit diagram of a second prior art circuit for creating a biphasic discharge into a heart.

FIG. 2 illustrates an example of a prior art circuit in which two capacitors arranged to act as a single capacitor create a biphasic shock. In the circuit of FIG. 2, four switches 206, 208, 216, and 218 control discharge of two capacitors 202 and 204 through electrodes 210 and 214 into heart 212. As with the circuit of FIG. 1, a charging circuit (not shown) charges capacitors 202 and 204. When these capacitors are sufficiently charged, switches 206 and 218 are closed, while switches 208 and 216 remain open. Capacitors 202 and 204, in series, begin to discharge, creating a current that flows from electrode 210 to electrode 214. When these capacitors have only partially discharged, switches 206 and 218 are opened. Shortly thereafter, switches 208 and 216 are closed. With switches 208 and 216 closed and switches 206 and 218 open, capacitor 204—but not capacitor 202—is charges. This creates a current that flows from electrode 214 to electrode 210.

The timing of the opening and the closing of the switches in FIGS. 1 and 2 is typically controlled using one of three general methods. The first is known as the fixed tilt method. Switches 104 and 116 or switches 206 and 218 are closed until the voltage on capacitor 102 or capacitors 202 and 204 falls below a predetermined level. Once the voltage on these capacitors falls to the predetermined level, switches 104 and 116 or switches 206 and 218 are opened. The second general method of controlling the switches is known as the fixed duration method. Switches 104 and 116 or switches 206 and 218 are closed for a predetermined period of time. Once the predetermined period of time expires, the switches are opened. The third general method of controlling the timing of the opening and closing of the switches is a hybrid of the fixed tilt method and the fixed duration method. Switches 104 and 116 or switches 206 and 218 are closed for a predetermined period of time that begins when the voltage on capacitor 102 or capacitors 202 and 204 falls below a predetermined level.

Because of the high voltages and currents required to defibrillate a heart, the switches in circuits such as those shown in FIGS. 1 and 2 must be rugged. In particular, they must be capable of "hot switching", i.e., closing and opening when there is a high voltage potential across the switch. Examples of switches that have been used in prior art devices include, but are not limited to, metal oxide semiconductor field effect transistors, insulated gate field effect transistors, insulated gate bipolar transistors, and silicon controlled rectifiers.

SUMMARY OF THE INVENTION

The present invention is directed to a discharge circuit for use in a multielectrode defibrillator or cardioverting device and methods of using such a circuit. The circuit includes at least two electrodes that are in electrical contact with a heart. Upon determination that a therapeutic shock needs to be applied to the heart, two capacitors configured for independent discharge are charged. Once these capacitors are sufficiently charged, one of the capacitors is switched such that it begins to discharge into the heart. At an appropriate time, this capacitor is switched again such that it no longer discharges into the heart. At this time, the other capacitor is switched such that it begins to discharge into the heart, and at the appropriate time, it is switched such that it stops discharging into the heart. The two capacitors are preferably configured with opposite polarities so that the waveform applied to the heart by the sequential discharging of the two capacitors is biphasic.

DETAILED DESCRIPTION OF THE PREFERRED EMBODIMENT

The present invention is directed to a discharge circuit for use in a multielectrode defibrillator or cardioverting device and methods of using such a circuit. The following descriptions of preferred embodiments of the method and apparatus are intended to be exemplary only. The invention is not limited to the exemplary embodiments or the manner in which the exemplary embodiments operate or are described herein. For purposes of the description and claims, cardioverting is intended to include delivery of high voltage therapy to any tachyarrhythmia including fibrillation and tachycardia.

Figure 3:
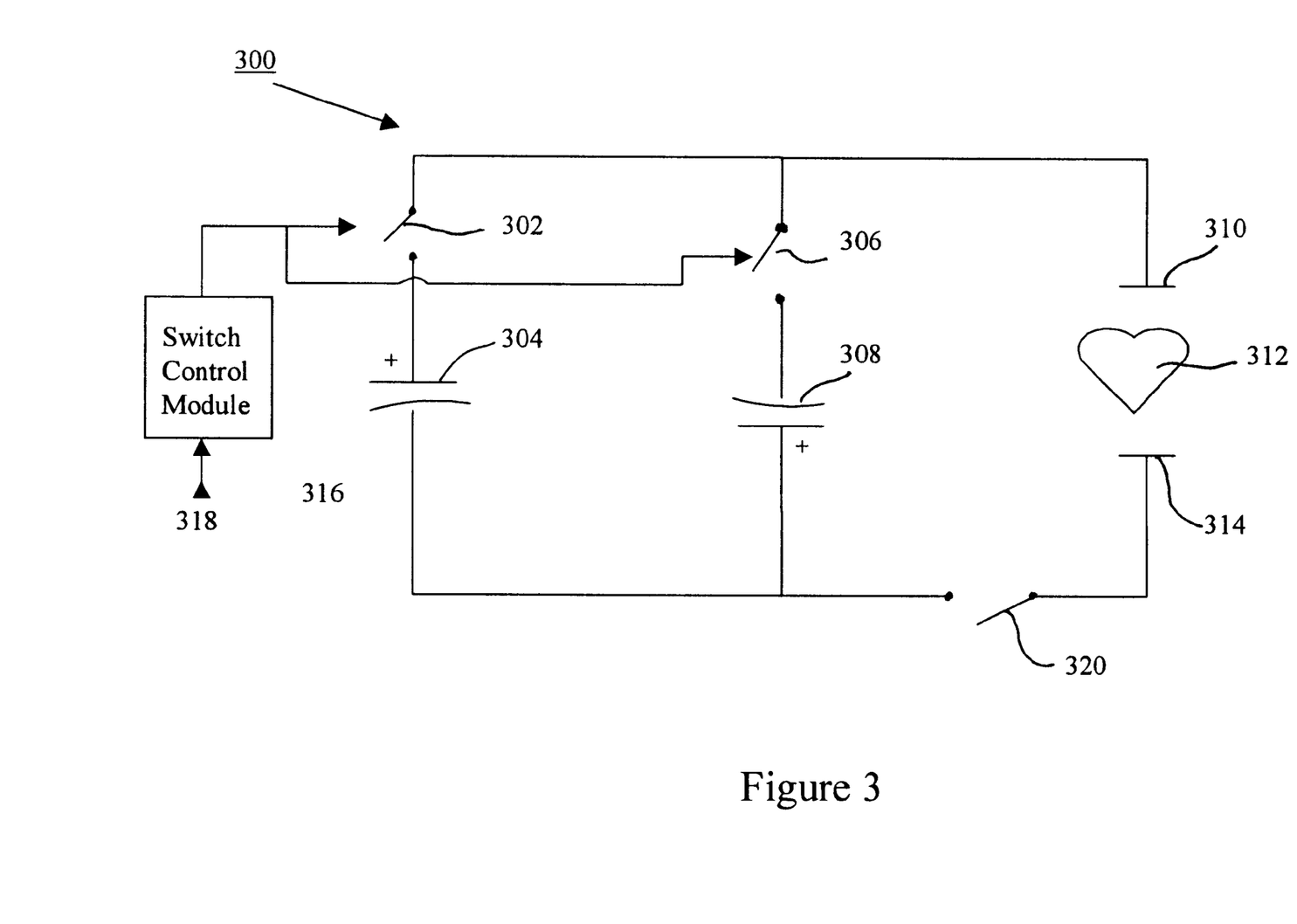
FIG. 3 illustrates an exemplary embodiment of the discharge circuit of the present invention.

FIG. 3 illustrates a first exemplary embodiment of the discharge circuit of the present invention. As shown, the circuit comprises two capacitors 304 and 308. Two electrodes 310 and 314 are electrically connected to heart 312. One plate of each of capacitors 304 and 308 is connected to electrode 314 via switch 320. Switches 302 and 306 connect the other plate of each of capacitors 304 and 308 to electrode 310. While switch 302 is closed (and switch 320 is also closed), capacitor 304 is electrically connected to electrodes 310 and 314. Any charge on capacitor 304 will discharge through electrodes 310 and 314 into heart 312. Likewise, while switch 306 is closed (and switch 320 is also closed), capacitor 308 is electrically connected to electrodes 310 and 314. Any charge on capacitor 308 will discharge through electrodes 310 and 314 into heart 312. A switch control module 316 controls switches 302 and 306. Switch 320 is provided to allow charging of capacitors 304 and 308. While switches 302, 306 and 320 are opened, capacitors 304 and 308 are charged in series from a suitable voltage source (not shown) such as a DC-to-DC converter as is known in the art. During discharge of capacitors 304 and 308, switch 320 is closed.

As shown in FIG. 3, capacitors 304 and 308 are preferably arranged with opposite polarities. That is, if capacitor 304 is arranged such that it discharges into electrode 310 creating current flow from electrode 310 to electrode 314, then capacitor 308 is arranged such that it discharges into electrode 314 creating current flow from electrode 314 to electrode 310. Alternatively, if capacitor 304 is arranged such that it discharges into electrode 314 creating current flow from electrode 314 to electrode 310, then capacitor 304 is arranged such it discharges into electrode 310 creating current flow from electrode 310 to electrode 314.

General operation of the circuit of FIG. 3 is as follows. Upon determination that a defibrillating shock needs to be delivered to heart 312, switch 320 is opened and switches 302 and 306 are open. A charging circuit (not shown) then charges capacitors 304 and 308. When capacitors 304 and 308 are sufficiently charged, the charging circuit is disconnected and switch 320 is closed. Thereafter, one of switches 302 or 306 is closed while the other switch is kept open. This causes the capacitor associated with the closed switch to discharge into the heart 312 through electrodes 310 and 314. Thereafter, the states of the switches 302 and 306 are reversed. That is, the previously closed switch is opened, and the previously open switch is closed. This causes the other capacitor to discharge into the heart 312 through electrodes 310 and 314. Because the capacitors 304 and 308 are arranged to have opposite polarities, the current flow caused by discharge of the second capacitor is opposite to the current flow caused by discharge of the first capacitor. Thereafter, the closed switch is opened, stopping the discharge of the capacitor. The waveform through heart 312 caused by operation of discharge circuit 300 is biphasic. At this point, switch 320 may be opened, with open being its default condition except during shock delivery.

The following is a specific example of the operation of the circuit of FIG. 3. Once the charging circuit (not shown) has sufficiently charged capacitors 304 and 308, the charging circuit is disconnected, switch 320 is closed and switch 302 is closed, while switch 306 remains open. This causes capacitor 304 to discharge into heart 312. Because of its polarity, capacitor 304 causes a current to flow from electrode 310 to electrode 314. Thereafter, switch 302 is opened, and capacitor 304 stops discharging. After a suitable safety delay, switch 306 is closed, which causes capacitor 308 to begin discharging into heart 312. Because the polarity of capacitor 308 is opposite the polarity of capacitor 304, capacitor 308 causes current to flow from electrode 314 to electrode 310. Thereafter, switch 306 is opened, which stops capacitor 308 from discharging. At this point, the defibrillating, biphasic electric shock has been delivered to heart 312.

Figure 4:
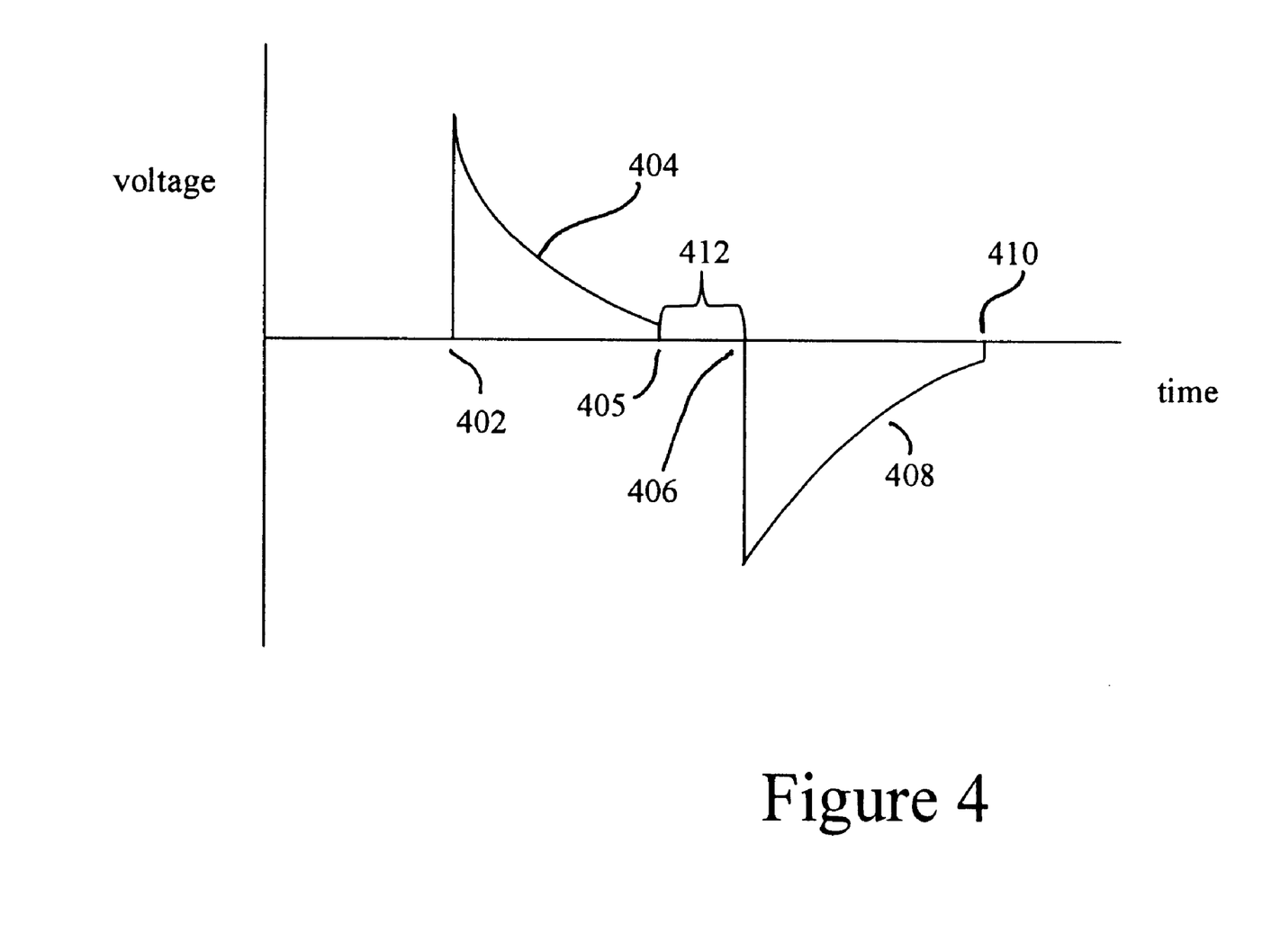
FIG. 4 illustrates an exemplary biphasic waveform generated by the circuit of FIG. 3.

FIG. 4 illustrates an exemplary waveform that may be generated by the circuit of FIG. 3 operating as described above. Time point 402 represents the point in time at which switch 302 is closed. (Capacitors 304 and 308 are charged prior to time point 402, and switch 320 is closed throughout the time period shown in FIG. 4.) The portion of the waveform 404 represents the voltage between electrodes 310 and 314 as capacitor 304 discharges. At time point 405, switch 302 is opened, and after a suitable delay 412, switch 306 is closed. Waveform portion 408 represents the voltage between electrodes 310 and 314 as capacitor 308 discharges. At time point 410, switch 306 is opened. It should be noted that switches 302 and 306 should never be closed at the same time. The delay 412 between opening of switch 302 and closing of switch 306 is for safety. This delay ensures that capacitors 304 and 306 will never discharge at the same time into heart 312. The delay should be sufficiently long to ensure that there will be no overlap of the discharge of capacitors 304 and 306. The waveform shown in FIG. 4 is generated between electrodes 310 and 314 and thus is applied to the heart 312. The waveform illustrated in FIG. 4 is exemplary only. The waveform illustrated in FIG. 4 assumes that capacitors 304 and 308 are equal in size and/or are charged to the same initial voltage level. The circuit of FIG. 3 may alternatively be configured and operated to generate many different waveforms.

Switch control module 316 may utilize any suitable method to control the timing of the closing and opening of switches 302 and 306. For example, the fixed tilt method may be used to determine how long to keep switch 302 closed. That is, a monitoring circuit (not shown) may monitor the voltage across capacitor 304. When the voltage has dropped below a predetermined level, switch 302 is opened and, after a suitable delay, switch 306 is closed. Alternatively, the fixed duration method may be used to control switch 302. That is, a timing circuit (not shown) may be used to keep switch 302 closed for a predetermined time period. Once the time period expires, switch 302 is opened and, after a suitable delay, switch 306 is closed. Of course the hybrid method may also be used. That is, a combination timing/monitoring circuit (not shown) may be used to operate switches 302 and 306 by closing the switch, monitoring the voltage on the corresponding capacitor until the voltage drops below a predetermined level and then waiting an additional predetermined period of time before opening the switch. Switch control module 316 may be specifically designed to implement one such method of controlling switches 302 and 306 or may be designed to implement more than one such method and to be programmable such that one method is programmably selected. A preferred method of controlling switches 302 and 306 is a 95% tilt method. Switch control module 316 may also include an input 318 that reverses the order in which capacitors 304 and 308 are discharged.

The capacitors 304 and 308 must be sufficiently large to deliver an electric shock capable of defibrillating the heart 312. Preferably, the sizes of capacitors 304 and 308 should also be chosen so as to deliver a defibrillating shock efficiently, that is, without requiring excess energy or voltage. The inventor believes that the following size combination are capable of delivering a defibrillating, biphasic shock in an efficient manner: capacitor 304 is 60 microfarads and capacitor 308 is 20 microfarads; capacitor 304 is 60 microfarads and capacitor 308 is 40 microfarads; and capacitor 304 is 90 microfarads and capacitor 308 is 30 microfarads. Variations of plus or minus 5 microfarads are considered to fall within these preferred combinations. The inventor also believes that a combination in which capacitor 304 and capacitor 308 are the same size is an advantageous combination. The invention is not, however, limited to the above described combinations. Rather, any combination of capacitor sizes capable of delivering a defibrillating shock sufficient to defibrillate a heart can be used with this invention.

Many types of switches are known for switching capacitors with high voltage charges such as are used in defibrillating devices. Such switches include, but are not limited to, metal oxide semiconductor field effect transistors, insulated gate field effect transistors, insulated gate bipolar transistors, and silicon controlled rectifiers. It should be noted that the circuit of FIG. 3 is preferably operated such that each capacitor 304 and 308 essentially fully discharges (e.g., at least 90% tilt) before its associated switch is opened to disconnect the capacitor from electrode 310.

Capacitors 304 and 308 are dischargable independently of each other. That is, capacitors 304 and 308 are not discharged at the same time. The order in which capacitors 304 and 308 discharge can easily be changed. That is, the switch control module 316 can be designed such that it is easily reconfigured either to cause capacitor 304 to discharge first followed by capacitor 308 or to cause capacitor 308 to discharge first followed by capacitor 304. For example, switch control module 316 may include an input 318 that toggles between sequentially discharging capacitor 304 first followed by capacitor 308 and sequentially discharging capacitor 308 first followed by capacitor 304. Specific designs for such control circuits are within the skill and knowledge of those who regularly practice in the field and will not be further described herein.

Figure 5:
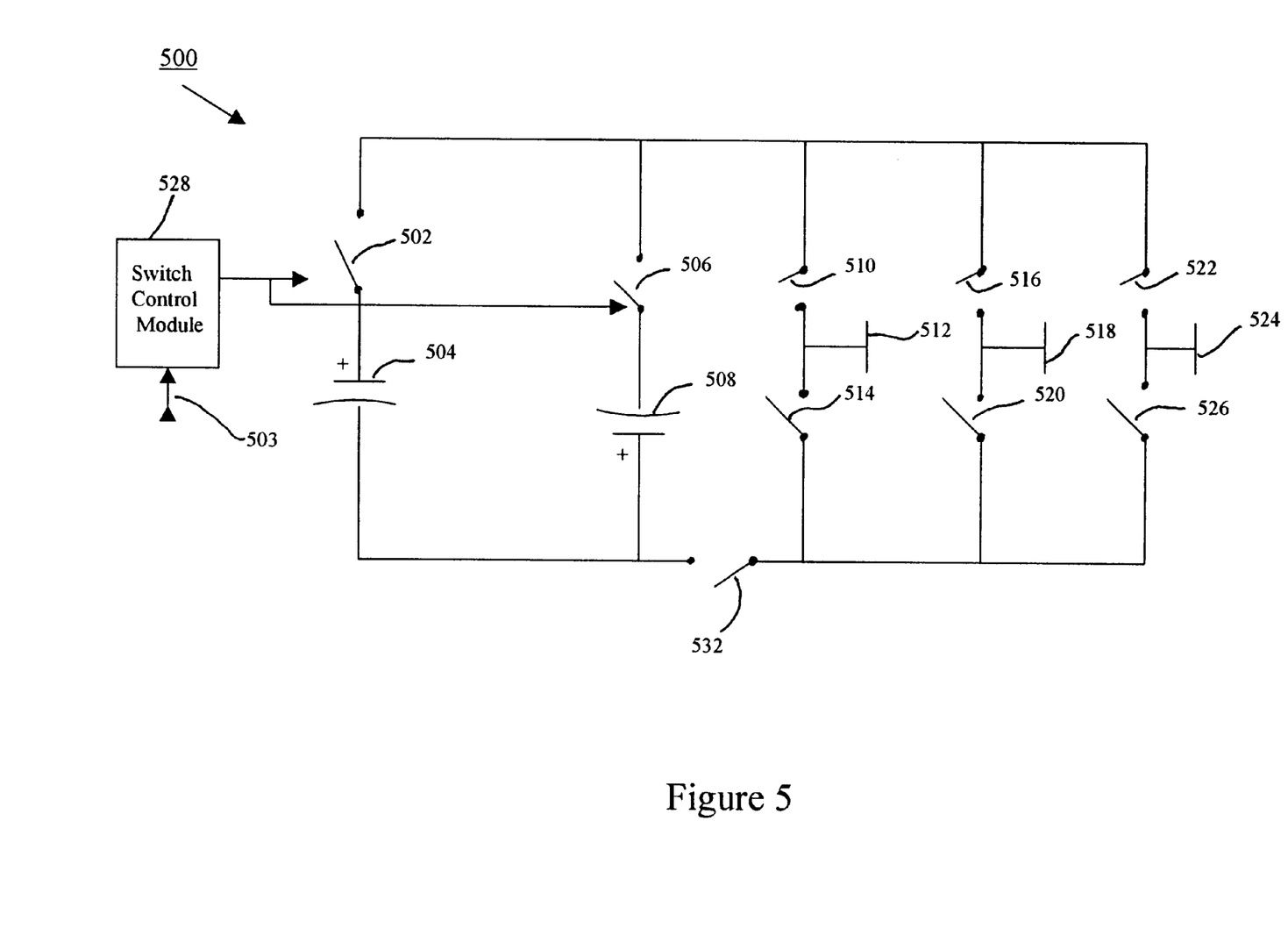
FIG. 5 illustrates another exemplary embodiment of the discharge circuit of the present invention.

FIG. 5 illustrates an alternative embodiment of the circuit of the present invention. In some ways, the circuit of FIG. 5 is similar to the circuit of FIG. 3. The circuit 500 of FIG. 5, like the circuit of FIG. 3, includes two capacitors 504 and 508 whose discharge is controlled by switches 502 and 506. Unlike the circuit of FIG. 3, however, the circuit of FIG. 5 includes three electrodes 512, 518, and 524 that are electrically connected to a heart (not shown). FIG. 5 also includes six switches 510, 514, 516, 520, 522, and 526 for selecting which of electrodes 512, 518, and 524 is selected and electrically connected to capacitors 504 and 508. Like switch 320 of FIG. 3, switch 532 is necessary for charging of capacitors 502 and 504.

Operation of FIG. 5 is as follows. A particular electrode configuration is selected and set using switches 510, 514, 516, 520, 522, and 526. For example, to deliver a defibrillating shock through the heart (not shown) between electrodes 512 and 518, switches 510 and 520 may be closed while switches 514, 516, 522, and 526 are open. Upon determination that a defibrillating shock needs to be delivered to the heart (not shown), switch 532 is opened and a charging circuit (not shown) then charges capacitors 504 and 508. When capacitors 504 and 508 are sufficiently charged, the charging circuit is disconnected and switch 532 is closed. Thereafter, one of switches 502 or 506 is closed while the other switch is kept open. For example, switch 502 might be closed while switch 506 is kept open. This causes the charge on capacitor 504 to begin discharging, creating a current flow through the heart (not shown) from electrode 512 to electrode 518. Thereafter, switch 502 is opened, which stops capacitor 504 from discharging. Then, after a suitable delay, switch 506 is closed, which causes the charge on capacitor 508 to begin discharging, creating a current flow through the heart (not shown) from electrode 518 to electrode 512. Thereafter, switch 506 is opened, which stops capacitor 508 from discharging. This operation creates a biphasic waveform applied to the heart (not shown) between electrodes 512 and 518. To reverse the relative polarities of the waveform, switches 514 and 516 can be closed while switches 510, 520, 522, and 526 are open. Alternatively, the relative polarities of the waveform can be reversed by reversing the order of discharge of the capacitors 504 and 508 such that capacitor 508 discharges first followed by capacitor 504. A switch control module 528 similar to the switch control module 316 of FIG. 3 may be used to control switches 502 and 506. Input 530 may be similar to input 318 of FIG. 3.

It is a simple matter to reconfigure the circuit to deliver the biphasic waveform created by the sequential discharging of capacitors 504 and 508 between different electrodes 512, 518, and 524. For example, to deliver the biphasic waveform between electrodes 518 and 524, switches 516 and 526 are closed, while switches 510, 514, 520, and 522 are open. Alternatively, switches 520 and 522 can be closed, while switches 510, 514, 516, and 526 are open. To deliver the biphasic waveform between electrodes 512 and 524, switches 510 and 526 are closed while switches 514, 516, 520, and 522 are open. Alternatively, switches 514 and 522 can be closed while switches 510, 516, 520, and 526 are open.

It is also possible to operate the three electrodes 512, 518, and 524 at the same time. For example, by closing switches 510, 516, and 526, while switches 514, 520, and 522 are open, the biphasic waveform created by the sequential discharging of capacitors 504 and 508 is delivered through electrodes 512 and 518 to electrode 524. Of course other electrode configurations can be selected by closing or opening switches 510, 514, 516, 520, 522, and 526.

Capacitors 504 and 508 may be the same sizes as described above with respect to FIG. 3. Likewise, switches 502 and 506 may be of the same types as switches 302 and 306 as described above with respect to FIG. 3. Switches 510, 514, 516, 520, 522, and 526 may likewise be the same type of switches as switches 302 and 306. Because switches 510, 514, 516, 520, 522, 526, and 532 are not "hot switched," that is, they are opened or closed before handling high voltages or high currents, these switches need not be capable of handling high voltage switching. Only switches 502 and 506 are required to handle high voltage switching. Moreover, additional switches can be added to accommodate additional electrodes.

Figure 6:
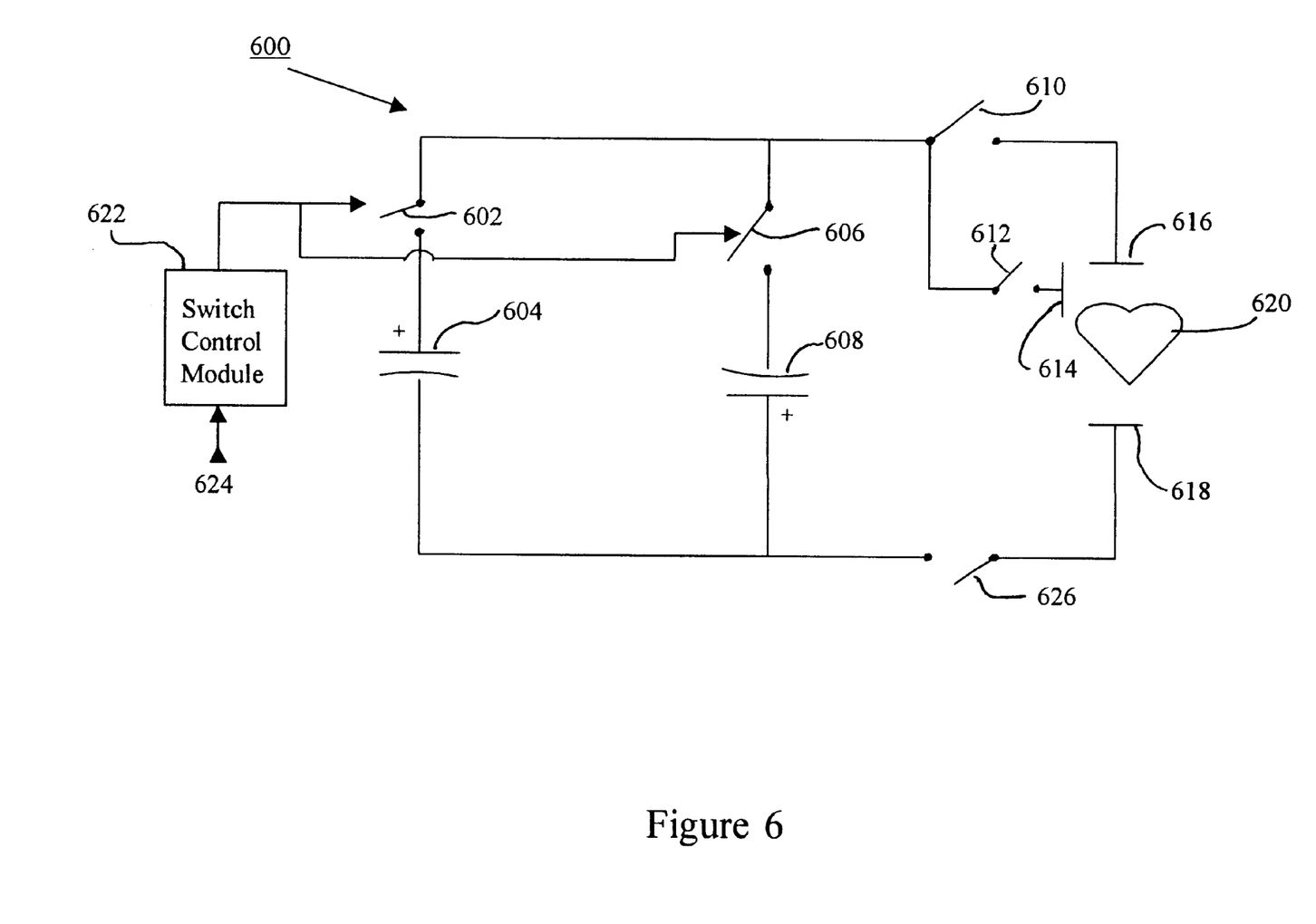
FIG. 6 illustrates yet another exemplary embodiment of the discharge circuit of the present invention.

FIG. 6 illustrates yet another embodiment of the discharge circuit of the present invention. This circuit 600 is similar to the circuits of FIGS. 3 and 5 in the sense that it includes two independently discharged capacitors 604 and 608 whose discharge is controlled by switches 602 and 606. Like the circuit of FIG. 5, the circuit of FIG. 6 includes three electrodes 614, 616, and 618. Switches 610 and 612 control whether the generated waveform will be applied to the heart 620 between electrodes 614 and 618, electrodes 616 and 618, or electrodes 614 and 616 (functioning as a single electrode) and electrode 618. Like switch 320 of FIG. 3, switch 626 is provided for charging of capacitors 604 and 608.

The operation of the circuit of FIG. 6 is similar to the operation of the circuit of FIG. 5. A particular electrode configuration is selected and set using switches 610 and 612. For example, to deliver a defibrillating shock through heart 620 between electrodes 614 and 618, switch 612 is closed and switch 610 is opened. To deliver a defibrillating shock through heart 620 between electrodes 616 and 618, switch 610 is closed and switch 612 is opened. To deliver a defibrillating shock through heart 620 between electrodes 614 and 616, functioning as a single electrode, and electrode 618, switches 610 and 612 are both closed. Upon determination that a defibrillating shock needs to be delivered to the heart 620, switch 626 is opened and a charging circuit (not shown) charges capacitors 604 and 608. When capacitors 604 and 608 are sufficiently charged, the charging circuit is disconnected and switch 626 is closed. Thereafter, one of switches 602 or 606 is closed while the other switch is kept open. For example, switch 602 might be closed while switch 606 is kept open. This causes the charge on capacitor 604 to begin discharging, creating a current flow through the heart 620 from electrode 614 to electrode 618, assuming that switch 612 is closed and switch 610 is open. Thereafter, switch 602 is opened, which stops capacitor 604 from discharging. Then, after a suitable delay, switch 606 is closed, which causes the charge on capacitor 608 to begin discharging, creating a current flow through the heart 620 from electrode 618 to electrode 614, again assuming that switch 612 is closed and switch 610 is open. Thereafter, switch 606 is opened, which stops capacitor 608 from discharging. This operation creates a biphasic waveform applied to the heart 620 between electrodes 614 and 618. A switch control module 622 similar to the switch control module 316 may be used to control switches 602 and 606. The relative polarities of the waveform applied to the heart 620 can be reversed by reversing the order of discharge of the capacitors 604 and 608 such that capacitor 608 discharges first followed by capacitor 604. Switch control module 622 may include an input 624 that reverses the order in which capacitors 604 and 608 are discharged.

It is a simple matter to reconfigure the circuit to deliver the biphasic waveform created by the sequential discharging of capacitors 604 and 608 between electrodes 616 and 618 rather than between electrodes 614 and 618. Initially, rather than close switch 612 and open switch 610, switch 610 is closed and switch 612 is opened. Thereafter, capacitor 604 is discharged by closing switch 602 and then capacitor 608 is discharged by closing switch 606 as described above. Because switch 610 is closed and switch 612 is open, the resulting biphasic waveform is applied to the heart 620 between electrodes 616 and 618. Likewise, it is a simple matter to reconfigure the circuit to deliver the biphasic waveform created by the sequential discharging of capacitors 604 and 608 between electrodes 614 and 616 (functioning as a single electrode) and electrode 618. Initially, switches 610 and 612 are both closed. Thereafter, capacitor 604 is discharged by closing switch 602 and then capacitor 608 is discharged by closing switch 606 as described above. Because switches 610 and 612 are both closed, the resulting biphasic waveform is applied to the heart 620 between electrodes 614 and 616 (functioning as a single electrode) and 618.

Capacitors 604 and 608 may be the same sizes as described above with respect to FIG. 3. Likewise, switches 602 and 606 may be of the same types as switches 302 and 306 as described above with respect to FIG. 3. Switches 610, 612 and 626 may likewise be the same type of switches as switches 510, 514, etc. Because switches 610, 612 and 626 are not "hot switched," these switches need not be capable of handling high voltage switching.

The above described embodiments of the invention are not intended to be limiting. Persons skilled in the art will appreciate that modifications may be made to these embodiments and alternative embodiments may be created that are within the scope and spirit of the invention. For example, although the above described embodiments are incorporated into a defibrillating device, the invention may alternatively be used in other types of cardioverting devices that deliver electric shocks to the heart to treat an electrical malfunction of the heart.

What is claimed is:

1. In a cardioverting device for applying a cardioverting shock to a heart, an apparatus comprising:

a first electrode for electrical contact with said heart, a second electrode for electrical contact with said heart, a first capacitor, a first plate of said first capacitor having a positive polarity and being electrically connected to said first electrode, a second capacitor, a first plate of said second capacitor having a negative polarity and being electrically connected to said first electrode, a first switch electrically connecting a second plate of said first capacitor to said second electrode, a second switch electrically connecting a second plate of said second capacitor to said second electrode, and a switch control module configured to control said first switch and said second switch such that said first capacitor and said second capacitor are independently discharged into said heart wherein current flows from said respective first and second capacitors through said first and second electrodes in opposite directions when said first and second switches are closed, wherein said first capacitor first plate and said second capacitor first plate are initially connected to a common node during at least a portion of the first current flow direction phase and are connected to the same node for at least a portion of the second current direction phase.

2. The apparatus of claim 1 and further including a third switch electrically connecting said first plates of said first and second capacitors to said first electrode.

3. The apparatus of claim 1, wherein a capacitance of said first capacitor is equal to a capacitance of said second capacitor.

4. The apparatus of claim 1, wherein a capacitance of said second capacitor is smaller than a capacitance of said first capacitor.

5. The apparatus of claim 1, wherein said switch control module comprises an input for setting a sequential order in which said first capacitor and said second capacitor are discharged.

6. The apparatus of claim 1, wherein said switch control module controls the closing of each of said first and second switches in sequence according to one of a fixed tilt method, a fixed duration method or a hybrid method.

7. The apparatus of claim 6, wherein said switch control module provides a predetermined safety time period following said opening of said first switch before said second switch is closed.

* * * * *